United States Patent [19]

Legoux et al.

[11] Patent Number: 5,700,665
[45] Date of Patent: Dec. 23, 1997

[54] METHOD FOR THE EXTRACTION OF PERIPLASMIC PROTEINS FROM PROKARYOTIC MICROORGANISMS IN THE PRESENCE OF ARGININE

[75] Inventors: Richard Legoux, Le Faget; Paul Maldonado, Symphorien d'Ozon; Marc Salome, Castanet Tolosan, all of France

[73] Assignee: Sanofi, Paris, France

[21] Appl. No.: 594,469

[22] Filed: Jan. 31, 1996

[30] Foreign Application Priority Data

Jan. 31, 1995 [FR] France ................. 95 01083

[51] Int. Cl.⁶ .............. C12N 1/20; C12N 1/21; C12P 21/00
[52] U.S. Cl. ............ 435/71.2; 435/69.4; 435/69.52; 435/252.3
[58] Field of Search .............. 435/69.1, 71.1, 435/71.2, 243, 252.3, 69.4, 69.52

[56] References Cited

FOREIGN PATENT DOCUMENTS

| 0 217 379 | 4/1987 | European Pat. Off. . |
| 0 360 641 | 3/1990 | European Pat. Off. . |
| 0 393 725 | 10/1990 | European Pat. Off. . |
| 88 10307 | 12/1988 | WIPO . |
| 92 22665 | 12/1992 | WIPO . |

OTHER PUBLICATIONS

Patent Abstracts of Japan, vol. 11 No. 246 (C–439), Aug. 11, 1987 & JP-A-62 051983 (Yoshihide Hagiwara) Mar. 6, 1987.

Patent Abstracts of Japan, vol. 11 No. 232 (C–437), 29 Juillet 1987 & JP-A-62 044198 (Hanaka Keizo) Feb. 26, 1987.

Dissertation Abstracts International B, vol. 37, No. 5, 1976 pp. 200–201, Brown et al. "Purification by Bioaffinity Chromatography of Two Arginine–Specific Periplasmic Binding Proteins".

*Primary Examiner*—George C. Elliott
*Assistant Examiner*—Robert Schwartzman
*Attorney, Agent, or Firm*—Bacon & Thomas

[57] ABSTRACT

The invention relates to a method for the extraction of recombinant periplasmic proteins wherein arginine is used as the extraction agent. In particular, the invention relates to a method for the extraction of a periplasmic protein of interest, which essentially consists in:

(i) suspending the pellet of cells or of cell debris from cells, which cells originate from the culture of a prokaryotic microorganism transformed with an expression vector containing a gene coding for the protein and means for its expression in the periplasm of the microorganism, in a buffer solution containing arginine; and (ii) recovering the protein of interest in the supernatant of the bacterial suspension thereby obtained.

18 Claims, No Drawings

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 4410 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 1:

-continued

| | | | | | |
|---|---|---|---|---|---|
|TCGAGTGGGT|TTGAGGCGAT|CACACTTCTG|TTAACGCAGA|ACCTAAACGC|ATCTCGACTG|60
|CACGGTGCAC|CAATGCTTCT|GGCGTCAGGC|AGCCATCGGA|AGCTGTGGTA|TGGCTGTGCA|120
|GGTCGTAAAT|CACTGCATAA|TTCGTGTCGC|TCAAGGCGCA|CTCCGTTCT|GGATAATGTT|180
|TTTTGCGCCG|ACATCATAAC|GGTTCTGGCA|AATATTCTGA|AATGAGCTGT|TTCGAGCTGA|240
|CTGACTGTTG|CTTATATTAC|ATCGATAGCG|TATAATGTGT|GGAATTGTGA|GCGGATAACA|300
|ATTTCACACA|GTTTTTCGCG|AAGAAGGAGA|TATACATATG|AAAAAGATCC|TGGCGTTAGC|360
|TGCGCTGACT|ACCGTTGTAT|TCTCTGCGTC|CGCCTTCGCT|GGCCCTGTGC|CTCCCAGTAC|420
|TGCCCTCAGG|GAGCTCATTG|AGGAGCTGGT|CAACATCACC|CAGAACCAGA|AGGCTCCGCT|480
|CTGCAATGGC|AGCATGGTAT|GGAGCATCAA|CCTGACAGCT|GGCATGTACT|GTGCAGCCCT|540
|GGAATCCCTG|ATCAACGTGT|CAGGCTGCAG|TGCCATCGAG|AAGACCCAGA|GGATGCTGAG|600
|CGGATTCTGC|CCGCACAAGG|TCTCAGCTGG|GCAGTTTTCC|AGCTTGCATG|TCGAGACAC|660
|CAAAATCGAG|GTGGCCCAGT|TTGTAAAGGA|CCTGCTCTTA|CATTTAAAGA|AACTTTTTCG|720
|CGAGGGACGG|TTCAACTGAA|ACTTCGAAAG|CATCATTATT|TGGGATCCGG|CTGCTAACAA|780
|AGCCCGAAAG|GAAGCTGAGT|TGGCTGCTGC|CACCGCTGAG|CAATAACTAG|CATAACCCCT|840
|TGGGGCCTCT|AAACGGGTCT|TGAGGGGTTT|TTTGCTGAAA|GGAGGAACTA|TATCCGGATG|900
|TACCAAGCTT|GGCCGGATCA|AAGTTTTGTC|GTCTTTCCAG|ACGTTAGTAA|ATGAATTTTC|960
|TGTATGAGGT|TTTGCTAAAC|AACTTTCAAC|AGTTTCAGCG|GAGTGAGAAT|AGAAAGGAAC|1020
|AACTAAAGGA|ATTGCGAATA|ATAATTTTTT|CACGTTGAAA|ATCTCCAAAA|AAAAAGGCTC|1080
|CAAAGGAGC|CTTTAATTGT|ATCGGTTTAT|CAGCTTGCTT|TCGAGGTGAA|TTTCTTAAAC|1140
|AGCTTGATAC|CGATAGTTGC|GCCGACAATG|ACAACAACCA|TCGCCCACGC|ATAACCGATA|1200
|TATTCGGTCG|CTGAGGCTTG|CAGGGAGTCA|AAGGCCGCTT|TTGCGGGATC|GATCCGCGGA|1260
|AGCATAAAGT|GTAAAGCCTG|GGGTGCCTAA|TGAGTGAGCT|AACTCACATT|AATTGCGTTG|1320
|CGCTCACTGC|CCGCTTTCCA|GTCGGGAAAC|CTGTCGTGCC|AGCTGCATTA|ATGAATCGGC|1380
|CAACGCGCGG|GGAGAGGCGG|TTTGCGTATT|GGGCGCCAGG|GTGGTTTTTC|TTTTCACCAG|1440
|TGAGACGGGC|AACAGCTGAT|TGCCCTTCAC|CGCCTGGCCC|TGAGAGAGTT|GCAGCAAGCG|1500
|GTCCACGCTG|GTTTGCCCCA|GCAGGCGAAA|ATCCTGTTTG|CTGGTGGTTA|ACGGCGGGAT|1560
|ATAACATGAG|CTGTCTTCGG|TATCGTCGTA|TCCCACTACC|GAGATATCCG|CACCAACGCG|1620
|CAGCCCGGAC|TCGGTAATGG|CGCGCATTGC|GCCCAGCGCC|ATCTGATCGT|TGGCAACCAG|1680
|CATCGCAGTG|GGAACGATGC|CCTCATTCAG|CATTTGCATG|GTTTGTTGAA|AACCGGACAT|1740
|GGCACTCCAG|TCGCCTTCCC|GTTCCGCTAT|CGGCTGAATT|TGATTGCGAG|TGAGATATTT|1800
|ATGCCAGCCA|GCCAGACGCA|GACGCGCCGA|GACAGAACTT|AATGGGCCCG|CTAACAGCGC|1860
|GATTTGCTGG|TGACCCAATG|CGACCAGATG|CTCCACGCCC|AGTCGCGTAC|CGTCTTCATG|1920
|GGAGAAAATA|ATACTGTTGA|TGGGTGTCTG|GTCAGAGACA|TCAAGAAATA|ACGCCGGAAC|1980
|ATTAGTGCAG|GCAGCTTCCA|CAGCAATGGC|ATCCTGGTCA|TCCAGCGGAT|AGTTAATGAT|2040
|CAGCCCACTG|ACGCGTTGCG|CGAGAAGATT|GTGCACCGCC|GCTTTACAGG|CTTCGACGCC|2100
|GCTTCGTTCT|ACCATCGACA|CCACCACGCT|GGCACCCAGT|TGATCGGCGC|GAGATTTAAT|2160
|CGCCGCGACA|ATTTGCGACG|GCGCGTGCAG|GGCCAGACTG|GAGGTGGCAA|CGCCAATCAG|2220
|CAACGACTGT|TTGCCCGCCA|GTTGTTGTGC|CACGCGGTTG|GGAATGTAAT|TCAGCTCCGC|2280
|CATCGCCGCT|TCCACTTTTT|CCCGCGTTTT|CGCAGAAACG|TGGCTGGCCT|GGTTCACCAC|2340
|GCGGGAAACG|GTCTGATAAG|AGACACCGGC|ATACTCTGCG|ACATCGTATA|ACGTTACTGG|2400

-continued

```
TTTCACATTC ACCACCCTGA ATTGACTCTC TTCCGGGCGC TATCATGCCA TACCGCGAAA     2460
GGTTTTGCGC CATTCGATCT ACGCCGGACG CATCGTGGCC GCAAACCAAC CCTTGGCAGA     2520
ACATATCCAT CGCGTCCGCC ATCTCCAGCA GCCGCACGCG GCGCATCTCG GCCGCGTTG      2580
CTGGCGTTTT TCCATAGGCT CCGCCCCCCT GACGAGCATC ACAAAAATCG ACGCTCAAGT     2640
CAGAGGTGGC GAAACCCGAC AGGACTATAA AGATACCAGG CGTTTCCCCC TGGAAGCTCC     2700
CTCGTGCGCT CTCCTGTTCC GACCCTGCCG CTTACCGGAT ACCTGTCCGC CTTTCTCCCT     2760
TCGGGAAGCG TGGCGCTTTC TCAATGCTCA CGCTGTAGGT ATCTCAGTTC GGTGTAGGTC     2820
GTTCGCTCCA AGCTGGGCTG TGTGCACGAA CCCCCCGTTC AGCCCGACCG CTGCGCCTTA     2880
TCCGGTAACT ATCGTCTTGA GTCCAACCCG GTAAGACACG ACTTATCGCC ACTGGCAGCA     2940
GCCACTGGTA ACAGGATTAG CAGAGCGAGG TATGTAGGCG GTGCTACAGA GTTCTTGAAG     3000
TGGTGGCCTA ACTACGGCTA CACTAGAAGG ACAGTATTTG GTATCTGCGC TCTGCTGAAG     3060
CCAGTTACCT TCGGAAAAAG AGTTGGTAGC TCTTGATCCG GCAAACAAAC CACCGCTGGT     3120
AGCGGTGGTT TTTTGTTTG CAAGCAGCAG ATTACGCGCA GAAAAAAGG ATCTCAAGAA       3180
GATCCTTTGA TCTTTTCTAC GGGGTCTGAC GCTCAGTGGA ACGAAAACTC ACGTTAAGGG     3240
ATTTTGGTCA TGAGATTATC AAAAAGGATC TTCACCTAGA TCCTTTTAAA TTAAAAATGA     3300
AGTTTTAAAT CAATCTAAAG TATATATGAG TAAACTTGGT CTGACAGTTA CCAATGCTTA     3360
ATCAGTGAGG CACCTATCTC AGCGATCTGT CTATTTCGTT CATCCATAGT TGCCTGACTC     3420
CCCGTCGTGT AGATAACTAC GATACGGGAG GGCTTACCAT CTGGCCCAG TGCTGCAATG     3480
ATACCGCGAG ACCCACGCTC ACCGGCTCCA GATTTATCAG CAATAAACCA GCCAGCCGGA     3540
AGGGCCGAGC GCAGAAGTGG TCCTGCAACT TTATCCGCCT CCATCCAGTC TATTAATTGT     3600
TGCCGGGAAG CTAGAGTAAG TAGTTCGCCA GTTAATAGTT TGCGCAACGT TGTTGCCATT     3660
GCTGCAGGCA TCGTGGTGTC ACGCTCGTCG TTTGGTATGG CTTCATTCAG CTCCGGTTCC     3720
CAACGATCAA GGCGAGTTAC ATGATCCCCC ATGTTGTGCA AAAAAGCGGT TAGCTCCTTC     3780
GGTCCTCCGA TCGTTGTCAG AAGTAAGTTG GCCGCAGTGT TATCACTCAT GGTTATGGCA     3840
GCACTGCATA ATTCTCTTAC TGTCATGCCA TCCGTAAGAT GCTTTTCTGT GACTGGTGAG     3900
TACTCAACCA AGTCATTCTG AGAATAGTGT ATGCGGCGAC CGAGTTGCTC TTGCCCGGCG     3960
TCAACACGGG ATAATACCGC GCCACATAGC AGAACTTTAA AAGTGCTCAT CATTGGAAAA     4020
CGTTCTTCGG GGCGAAAACT CTCAAGGATC TTACCGCTGT TGAGATCCAG TTCGATGTAA     4080
CCCACTCGTG CACCCAACTG ATCTTCAGCA TCTTTTACTT TCACCAGCGT TTCTGGGTGA     4140
GCAAAAACAG GAAGGCAAAA TGCCGCAAAA AAGGGAATAA GGGCGACACG GAAATGTTGA     4200
ATACTCATAC TCTTCCTTTT TCAATATTAT TGAAGCATTT ATCAGGGTTA TTGTCTCATG     4260
AGCGGATACA TATTTGAATG TATTTAGAAA AATAAACAAA TAGGGGTTCC GCGCACATTT     4320
CCCCGAAAAG TGCCACCTGA CGTCTAAGAA ACCATTATTA TCATGACATT AACCTATAAA     4380
AATAGGCGTA TCACGAGGCC CTTTCGTCCC                                     4410
```

( 2 ) INFORMATION FOR SEQ ID NO: 2:

( i ) SEQUENCE CHARACTERISTICS:
        ( A ) LENGTH: 282 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 2:

| | | | | | |
|---|---|---|---|---|---|
| TCGAGTGGGT | TTGAGGCGAT | CACACTTCTG | TTAACGCAGA | ACCTAAACGC | ATCTCGACTG | 60
| CACGGTGCAC | CAATGCTTCT | GGCGTCAGGC | AGCCATCGGA | AGCTGTGGTA | TGGCTGTGCA | 120
| GGTCGTAAAT | CACTGCATAA | TTCGTGTCGC | TCAAGGCGCA | CTCCCGTTCT | GGATAATGTT | 180
| TTTTGCGCCG | ACATCATAAC | GGTTCTGGCA | AATATTCTGA | AATGAGCTGT | TTCGAGCTGA | 240
| CTGACTGTTG | CTTATATTAC | ATCGATAGCG | TATAATGTGT | GG | | 282

( 2 ) INFORMATION FOR SEQ ID NO: 3:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 3:

| | | | | | |
|---|---|---|---|---|---|
| AATTGTGAGC | GGATAACAAT | TTCACACAGT | TTTTCGCGAA | GAAGGAGATA | TACAT | 55

( 2 ) INFORMATION FOR SEQ ID NO: 4:

( i ) SEQUENCE CHARACTERISTICS:
        ( A ) LENGTH: 425 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 4:

| | | | | | |
|---|---|---|---|---|---|
| ATGAAAAAGA | TCCTGGCGTT | AGCTGCGCTG | ACTACCGTTG | TATTCTCTGC | GTCCGCCTTC | 60
| GCTGGCCCTG | TGCCTCCCAG | TACTGCCCTC | AGGGAGCTCA | TTGAGGAGCT | GGTCAACATC | 120
| ACCCAGAACC | AGAAGGCTCC | GCTCTGCAAT | GGCAGCATGG | TATGGAGCAT | CAACCTGACA | 180
| GCTGGCATGT | ACTGTGCAGC | CCTGGAATCC | CTGATCAACG | TGTCAGGCTG | CAGTGCCATC | 240
| GAGAAGACCC | AGAGGATGCT | GAGCGGATTC | TGCCCGCACA | AGGTCTCAGC | TGGGCAGTTT | 300
| TCCAGCTTGC | ATGTCCGAGA | CACCAAAATC | GAGGTGGCCC | AGTTTGTAAA | GGACCTGCTC | 360
| TTACATTTAA | AGAAACTTTT | TCGCGAGGGA | CGGTTCAACT | GAAACTTCGA | AAGCATCATT | 420
| ATTTG | | | | | | 425

( 2 ) INFORMATION FOR SEQ ID NO: 5:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 5:

| | | | | |
|---|---|---|---|---|
| GGATCCGGCT | GCTAACAAAG | CCCGAAAGGA | AGCTGAGTTG | GCTGCTGCCA | 50

( 2 ) INFORMATION FOR SEQ ID NO: 6:

( i ) SEQUENCE CHARACTERISTICS:
        ( A ) LENGTH: 200 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 6:

| | | | | | |
|---|---|---|---|---|---|
| CCGCTGAGCA | ATAACTAGCA | TAACCCCTTG | GGGCCTCTAA | ACGGGTCTTG | AGGGGTTTTT | 60 |
| TGCTGAAAGG | AGGAACTATA | TCCGGATGTA | CCAAGCTTGG | CCGGATCAAA | GTTTGTCGT | 120 |
| CTTTCCAGAC | GTTAGTAAAT | GAATTTTCTG | TATGAGGTTT | TGCTAAACAA | CTTTCAACAG | 180 |
| TTTCAGCGGA | GTGAGAATAG | | | | | 200 |

( 2 ) INFORMATION FOR SEQ ID NO: 7:

( i ) SEQUENCE CHARACTERISTICS:
        ( A ) LENGTH: 241 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 7:

| | | | | | |
|---|---|---|---|---|---|
| AAAGGAACAA | CTAAAGGAAT | TGCGAATAAT | AATTTTTTCA | CGTTGAAAAT | CTCCAAAAAA | 60 |
| AAAGGCTCCA | AAAGGAGCCT | TTAATTGTAT | CGGTTTATCA | GCTTGCTTTC | GAGGTGAATT | 120 |
| TCTTAAACAG | CTTGATACCG | ATAGTTGCGC | CGACAATGAC | AACAACCATC | GCCCACGCAT | 180 |
| AACCGATATA | TTCGGTCGCT | GAGGCTTGCA | GGGAGTCAAA | GGCCGCTTTT | GCGGGATCGA | 240 |
| T | | | | | | 241 |

( 2 ) INFORMATION FOR SEQ ID NO: 8:

( i ) SEQUENCE CHARACTERISTICS:
        ( A ) LENGTH: 1252 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 8:

| | | | | | |
|---|---|---|---|---|---|
| CCGCGGAAGC | ATAAAGTGTA | AAGCCTGGGG | TGCCTAATGA | GTGAGCTAAC | TCACATTAAT | 60 |
| TGCGTTGCGC | TCACTGCCCG | CTTTCCAGTC | GGGAAACCTG | TCGTGCCAGC | TGCATTAATG | 120 |
| AATCGGCCAA | CGCGCGGGGA | GAGGCGGTTT | GCGTATTGGG | CGCCAGGGTG | GTTTTCTTT | 180 |
| TCACCAGTGA | GACGGGCAAC | AGCTGATTGC | CCTTCACCGC | CTGGCCCTGA | GAGAGTTGCA | 240 |
| GCAAGCGGTC | CACGCTGGTT | TGCCCCAGCA | GGCGAAAATC | CTGTTTGCTG | GTGGTTAACG | 300 |
| GCGGGATATA | ACATGAGCTG | TCTTCGGTAT | CGTCGTATCC | CACTACCGAG | ATATCCGCAC | 360 |
| CAACGCGCAG | CCCGGACTCG | GTAATGGCGC | GCATTGCGCC | CAGCGCCATC | TGATCGTTGG | 420 |
| CAACCAGCAT | CGCAGTGGGA | ACGATGCCCT | CATTCAGCAT | TGCATGGTT | TGTTGAAAAC | 480 |
| CGGACATGGC | ACTCCAGTCG | CCTTCCCGTT | CCGCTATCGG | CTGAATTTGA | TTGCGAGTGA | 540 |
| GATATTTATG | CCAGCCAGCC | AGACGCAGAC | GCGCCGAGAC | AGAACTTAAT | GGGCCCGCTA | 600 |
| ACAGCGCGAT | TTGCTGGTGA | CCCAATGCGA | CCAGATGCTC | CACGCCCAGT | CGCGTACCGT | 660 |
| CTTCATGGGA | GAAAATAATA | CTGTTGATGG | GTGTCTGGTC | AGAGACATCA | AGAAATAACG | 720 |
| CCGGAACATT | AGTGCAGGCA | GCTTCCACAG | CAATGGCATC | CTGGTCATCC | AGCGGATAGT | 780 |
| TAATGATCAG | CCCACTGACG | CGTTGCGCGA | GAAGATTGTG | CACCGCCGCT | TTACAGGCTT | 840 |
| CGACGCCGCT | TCGTTCTACC | ATCGACACCA | CCACGCTGGC | ACCCAGTTGA | TCGGCGCGAG | 900 |
| ATTTAATCGC | CGCGACAATT | TGCGACGGCG | CGTGCAGGGC | CAGACTGGAG | GTGGCAACGC | 960 |

| | | | | | |
|---|---|---|---|---|---|
|CAATCAGCAA|CGACTGTTTG|CCCGCCAGTT|GTTGTGCCAC|GCGGTTGGGA|ATGTAATTCA 1020|
|GCTCCGCCAT|CGCCGCTTCC|ACTTTTTCCC|GCGTTTTCGC|AGAAACGTGG|CTGGCCTGGT 1080|
|TCACCACGCG|GGAAACGGTC|TGATAAGAGA|CACCGGCATA|CTCTGCGACA|TCGTATAACG 1140|
|TTACTGGTTT|CACATTCACC|ACCCTGAATT|GACTCTCTTC|CGGGCGCTAT|CATGCCATAC 1200|
|CGCGAAAGGT|TTTGCGCCAT|TCGATCTACG|CCGGACGCAT|CGTGGCCGCA|AA 1252|

(2) INFORMATION FOR SEQ ID NO: 9:

(i) SEQUENCE CHARACTERISTICS:
    (A) LENGTH: 1905 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 9:

| | | | | | |
|---|---|---|---|---|---|
|CCAACCCTTG|GCAGAACATA|TCCATCGCGT|CCGCCATCTC|CAGCAGCCGC|ACGCGGCGCA 60|
|TCTCGGGCCG|CGTTGCTGGC|GTTTTCCAT|AGGCTCCGCC|CCCTGACGA|GCATCACAAA 120|
|AATCGACGCT|CAAGTCAGAG|GTGGCGAAAC|CGACAGGAC|TATAAAGATA|CCAGGCGTTT 180|
|CCCCCTGGAA|GCTCCCTCGT|GCGCTCTCCT|GTTCCGACCC|TGCCGCTTAC|CGGATACCTG 240|
|TCCGCCTTTC|TCCCTTCGGG|AAGCGTGGCG|CTTTCTCAAT|GCTCACGCTG|TAGGTATCTC 300|
|AGTTCGGTGT|AGGTCGTTCG|CTCCAAGCTG|GGCTGTGTGC|ACGAACCCCC|CGTTCAGCCC 360|
|GACCGCTGCG|CCTTATCCGG|TAACTATCGT|CTTGAGTCCA|ACCCGGTAAG|ACACGACTTA 420|
|TCGCCACTGG|CAGCAGCCAC|TGGTAACAGG|ATTAGCAGAG|CGAGGTATGT|AGGCGGTGCT 480|
|ACAGAGTTCT|TGAAGTGGTG|GCCTAACTAC|GGCTACACTA|GAAGGACAGT|ATTTGGTATC 540|
|TGCGCTCTGC|TGAAGCCAGT|TACCTTCGGA|AAAAGAGTTG|GTAGCTCTTG|ATCCGGCAAA 600|
|CAAACCACCG|CTGGTAGCGG|TGGTTTTTTT|GTTTGCAAGC|AGCAGATTAC|GCGCAGAAAA 660|
|AAAGGATCTC|AAGAAGATCC|TTTGATCTTT|TCTACGGGGT|CTGACGCTCA|GTGGAACGAA 720|
|AACTCACGTT|AAGGGATTTT|GGTCATGAGA|TTATCAAAAA|GGATCTTCAC|CTAGATCCTT 780|
|TTAAATTAAA|AATGAAGTTT|TAAATCAATC|TAAAGTATAT|ATGAGTAAAC|TTGGTCTGAC 840|
|AGTTACCAAT|GCTTAATCAG|TGAGGCACCT|ATCTCAGCGA|TCTGTCTATT|TCGTTCATCC 900|
|ATAGTTGCCT|GACTCCCCGT|CGTGTAGATA|ACTACGATAC|GGGAGGGCTT|ACCATCTGGC 960|
|CCCAGTGCTG|CAATGATACC|GCGAGACCCA|CGCTCACCGG|CTCCAGATTT|ATCAGCAATA 1020|
|AACCAGCCAG|CCGGAAGGGC|CGAGCGCAGA|AGTGGTCCTG|CAACTTTATC|CGCCTCCATC 1080|
|CAGTCTATTA|ATTGTTGCCG|GGAAGCTAGA|GTAAGTAGTT|CGCCAGTTAA|TAGTTTGCGC 1140|
|AACGTTGTTG|CCATTGCTGC|AGGCATCGTG|GTGTCACGCT|CGTCGTTTGG|TATGGCTTCA 1200|
|TTCAGCTCCG|GTTCCCAACG|ATCAAGGCGA|GTTACATGAT|CCCCCATGTT|GTGCAAAAAA 1260|
|GCGGTTAGCT|CCTTCGGTCC|TCCGATCGTT|GTCAGAAGTA|AGTTGGCCGC|AGTGTTATCA 1320|
|CTCATGGTTA|TGGCAGCACT|GCATAATTCT|CTTACTGTCA|TGCCATCCGT|AAGATGCTTT 1380|
|TCTGTGACTG|GTGAGTACTC|AACCAAGTCA|TTCTGAGAAT|AGTGTATGCG|GCGACCGAGT 1440|
|TGCTCTTGCC|CGGCGTCAAC|ACGGGATAAT|ACCGCGCCAC|ATAGCAGAAC|TTTAAAAGTG 1500|
|CTCATCATTG|GAAAACGTTC|TTCGGGGCGA|AAACTCTCAA|GGATCTTACC|GCTGTTGAGA 1560|
|TCCAGTTCGA|TGTAACCCAC|TCGTGCACCC|AACTGATCTT|CAGCATCTTT|TACTTTCACC 1620|
|AGCGTTTCTG|GGTGAGCAAA|AACAGGAAGG|CAAAATGCCG|CAAAAAAGGG|AATAAGGGCG 1680|
|ACACGGAAAT|GTTGAATACT|CATACTCTTC|CTTTTTCAAT|ATTATTGAAG|CATTTATCAG 1740|

| | | | | | | |
|---|---|---|---|---|---|---|
| GGTTATTGTC | TCATGAGCGG | ATACATATTT | GAATGTATTT | AGAAAAATAA | ACAAATAGGG | 1800 |
| GTTCCGCGCA | CATTTCCCCG | AAAAGTGCCA | CCTGACGTCT | AAGAAACCAT | TATTATCATG | 1860 |
| ACATTAACCT | ATAAAAATAG | GCGTATCACG | AGGCCCTTTC | GTCCC | | 1905 |

METHOD FOR THE EXTRACTION OF PERIPLASMIC PROTEINS FROM PROKARYOTIC MICROORGANISMS IN THE PRESENCE OF ARGININE

The present invention relates to the extraction of recombinant proteins produced by prokaryotic microorganisms, especially by *E. coli*.

Increasing use is being made of genetic engineering techniques for the production of proteins of interest such as, for example, insulin, interleukins, growth hormone, and the like.

Generally, the microorganism is transformed with an expression vector containing a gene coding for the protein of interest and means needed for its expression such as the regulator signals. The microorganism is then cultured on a suitable culture medium and according to suitable culture parameters and, when a sufficient number of microorganism cells has been arrived at, the addition of an inducer triggers the so-called expression phase, during which the desired protein is produced at high level and accumulates. On completion of culturing, the cells in suspension are separated from the culture medium, for example by centrifugation or microfiltration, and are then subjected to an extraction method which frequently begins with an operation of disrupting of the walls of the microorganisms.

The expression of a gene coding for a protein of interest in a prokaryotic microorganism can be cytoplasmic, periplasmic or secretory, depending on the nature of the means of expression employed with the said gene (promoter, terminator, ribosome binding site, signal peptide, and the like).

Cytoplasmic expression enables large amounts of proteins to be obtained. However, prior to the extraction of the protein of interest, it is necessary, for proteins comprising one or more disulphide bridges, to carry out a step of denaturation/renaturation, which represents an especially cumbersome and intricate step during production on an industrial scale. The denaturation/renaturation step is carried out according to traditional means well known to a person skilled in the art, using a denaturing agent in the presence of a reducing agent followed by renaturation conditions comprising, in particular, a monitoring of the redox state of the solution. Among denaturing agents used, most particular mention must be made of guanidine hydrochloride, which has been proposed in a method for obtaining human interleukin-2. To this end, reference may be made, for example, to the document EP-A2-0,145,390.

With Gram-negative bacteria, little or no use has been made of secretory expression systems in which the protein of interest is to be found actively in the culture medium, on account of their low productivity. It should be noted here that the medium of a bacterial culture at high density in a bioreactor is not an ideal residence place for sensitive recombinant proteins on account, for example, of the risks of interfacial denaturation.

Periplasmic expression enables recombinant proteins which are, in principle, correctly folded to be obtained directly in a space protected from the environment and, as a result, represents a judicious choice for obtaining proteins, in particular unglycosylated proteins. In this case, it is hence not necessary to subject the proteins to a denaturation/renaturation step.

The methods of cell disruption generally used in this field are, for example, cell lysis by sonication or by mechanical pressure (French Pressure Cell, ball mill), chemical lysis or enzymatic lysis, osmotic shock and treatment using chaotropic agents or detergents. These methods disrupt the majority of cell membranes, including the plasma membranes and membranes of the endoplasmic reticulum, to form a homogeneous suspension of cell debris. The nature of the pellet of cell debris which can be harvested in general after centrifugation (nuclei, cytoskeleton, mitochondria, lysosomes, ribosomes, macromolecules, and the like) is dependent especially on the time and the speed of centrifugation (10 minutes at 1000 g to 3 hours at 150,000 g).

The difficulties encountered during the extraction operations vary according to the type of expression and the extraction methods used, and are, in particular:

loss in yield of the recombinant protein loss of biological activity of the recombinant protein proteolytic degradation of the recombinant protein toxicity of the extraction agents and obligatory monitoring of their removal difficulty of industrial implementation mixing of the periplasmic proteins with cytoplasmic proteins.

Furthermore, when the proteins of interest produced are hydrophobic or charged, they may associate with cell components which are themselves hydrophobic or charged, thereby rendering extraction especially difficult.

Considerable benefit might accrue from under-taking the industrial production of recombinant proteins of interest by genetic engineering, but this necessitates the development of extraction methods which avoid or minimize the above drawbacks.

In effect, it is not only important to produce large amounts of protein of interest, but these proteins must also not be contaminated with the extraction agents and must retain their full biological activity.

Various methods have been proposed for this purpose, especially for the extraction/separation of interleukin-2.

The document EP-A2-0,145,390 describes a method for obtaining unglycosylated human interleukin-2 (IL-2) having a specific activity of greater than 104 U/mg, which employs a step of separation by column chromatography to extract the IL-2. This method also involves a denaturation step using guanidine hydrochloride.

The document EP-A2-0,147,819 proposes a method for obtaining homogeneous and pure recombinant interleukin-2. This method consists in culturing a microorganism transformed by means of an expression vector containing the gene coding for interleukin-2, in causing lysis of the cells, in recovering the cell debris, in extracting the IL-2 by washing the cell debris with a suitable washing solution and then in purifying the washing solution by chromatography. The washing solutions used can contain a salt such as sodium chloride or guanidine hydrochloride, or a detergent such as, for example, the product known under the trade name "Triton X®-100".

According to a preferred variant, the successive use of three washing solutions, namely a washing solution containing sodium chloride, a washing solution containing a detergent and a washing solution containing guanidine hydrochloride, is recommended.

The document EP-A1-0,337,243 describes a method for purifying human interleukin-2 which utilizes a system of two reversed-phase liquid chromatography columns. Before the step of purification by chromatography the insoluble fraction of the bacterial cell lysate is extracted with a solution containing guanidine hydrochloride to obtain a bacterial extract, which is then diluted using a guanidine hydrochloride-free buffer and thereafter chromatographed, elution being carried out with an acetonitrile gradient.

It has now been found, surprisingly, that the extraction of a protein of interest produced by a prokaryotic microorganism, transformed with an expression vector containing a gene coding for the protein of interest and means for its expression such as the regulator signals needed for its periplasmic expression, may be carried out by suspending the pellet of cells or of cell debris from the microorganism, originating from the culture of the said microorganism, in a buffer solution, the said solution advantageously containing arginine, it being possible for the arginine to be in the L and/or D form.

According to a first aspect, the subject of the invention is the use of arginine as an agent for the extraction of periplasmic proteins.

According to another aspect, the subject of the present invention is a method for the extraction of a periplasmic protein of interest, which consists in:

1) suspending the pellet of cells originating from the culture of a microorganism, transformed with an expression vector containing a gene coding for the said protein and all the regulator signals needed for its periplasmic expression, in a buffer solution containing arginine and, after a period of contact under appropriate pH, temperature, bacterial concentration, and the like, conditions, 2) recovering the protein of interest in the supernatant of the bacterial suspension thereby obtained.

A variant of the said method for the extraction of a periplasmic protein of interest consists in suspending the pellet of cell debris, obtained after lysis of the cells originating from the culture, in the buffer solution containing arginine.

Extraction of the periplasmic proteins is especially efficient when the extraction buffer consists of an aqueous solution containing arginine at a concentration equal to at least 0.4M arginine within the limit of solubility of arginine at room temperature in water (in the region of 0.8M in pure water and above this in the presence of salts), and when its pH is slightly alkaline, preferably equal to 8.

Arginine is a natural α-amino acid which has been proposed as an auxiliary agent for the denaturation/renaturation/substitution of two chains of Abbokinase® (urinary plasminogen activator), in which chains a native peptide is partially replaced by a synthetic peptide during this operation. To this end, reference may be made to the paper by GA. Homandberg and T. Wai in Biochimica et Biophysica Acta, 1990, 1038, 209–215.

In the method of the invention or its variant, denaturation/renaturation of the protein is not carried out and the arginine participates only in respect of the extraction of a protein from a pellet of cells or of cell debris from microorganisms.

Arginine brings about noteworthy effects on the extraction of the protein, in respect of both the yield and the biological activity of the protein. It was, in effect, found that, for example, the mature form of IL-13 is recovered with the method of the invention in yields of greater than 95% while retaining the biological activity of the molecule. It should be noted that trials of extraction by osmotic shock on the same expression system do not lead to comparable yields.

Comparative trials showed that guanidine. HCl used under the same conditions also enables the IL-13 protein to be recovered in a yield of greater than 95% but, in contrast, the biological activity of the protein thus recovered is impaired more than by the arginine method.

While it is not wished to limit interpretation to some particular theory, arginine is thought to act as a mild and biological chaotropic agent, as opposed to the powerful chaotropic agents which are denaturing at the high concentrations needed, equal to or greater than 5M, in order to effect extraction, such as guanidine hydrochloride.

The method of the invention or its variant may be carried out following any method of culture of a microorganism transformed with an expression vector containing a gene coding for the protein of interest and means for a periplasmic expression of the said protein, such as all the necessary regulator signals.

It is obvious to a person skilled in the art that the method is applicable to bacteria closely related to *E. coli*, that is to say to so-called facultative anaerobic Gram-negative bacteria which constitute the Enterobacteriaceae group. In this family Enterobacteriaceae, the following species are to be found in particular: Escherichia, Salmonella, Erwinia and also Shigella, Klebsiella, Serratia, Proteus and Enterobacter.

Bearing in mind the chaotropic character of arginine, it is also apparent that arginine can, depending on the case, advantageously substitute for other chaotropic agents. Without it being possible to exemplify on all the families of bacteria on account of the diversity of the living systems in question, a person skilled in the art will know how to apply and adapt the arginine extraction method to his particular case.

Such culture methods are well known to a person skilled in the art. Methods describing the fermenter culture of Gram-negative bacteria are described, for example, in Patent EP-360,641 and EP-356,335 reporting the obtaining and use of the *E. coli* strains known as SEBR 1250 and TP 2339.

When the desired number of cells has been arrived at, the culture is subjected to a centrifugation (in general) or a microfiltration, and the pellet of biomass obtained is brought into contact with a buffer solution containing arginine according to the method of the invention.

As a general rule, the procedure is performed at a temperature between room temperature of approximately 25° C. and 2° C., preferably at 4° C.

The contact time of the cell pellet with the buffer solution containing arginine must be sufficient to permit passage of the protein of interest into the buffer solution.

In general, when the procedure is performed at 4° C., the contact time is advantageously approximately 1 hour.

The extraction, that is to say passage of the periphasmic protein into the medium, continues during the period of contact of the biomass and the arginine-containing extraction buffer. The contact time providing for complete extraction or an extraction showing no further change in level is between 30 minutes and 16 hours. Trials show that satisfactory extraction yields may be obtained in the space of a few hours at a temperature of 4° C. It has also been noted that gentle stirring of the biomass in its extraction buffer so as to avoid sedimentation of the pellet of microorganisms gives superior results, that is to say higher levels of extraction as a function of time.

The extraction method according to the invention is suitable for extracting both hydrophobic proteins such as, for example, interleukins, especially IL-13 described in the document EP-A1-0,506,574, and hydrophilic proteins such as, for example, growth hormone (hGH). The method of the invention simplifies the obtaining of hGH, which normally necessitates the use of an osmotic shock for its extraction.

To carry out the extraction of the protein of interest directly on the suspension of the cell pellet, a buffer solution containing arginine at a concentration of between 0.4M and 0.8M will be preferred.

When it is desired to carry out the extraction of the periplasmic protein of interest on the pellet of cell debris according to the variant of the method of the invention, the procedure is the same as is used in the method of the invention up to the step of obtaining the cell pellet obtained after centrifugation or microfiltration, and disruption of the cells is then performed according to methods well known to a person skilled in the art. Methods of cell disruption are described, for example, in C. T. Choma and H. Yamazaki, Can. J. Microbiol., 1981, 27, 547–550; L. O. Ingram, Journal of Bacteriology, 1981, 146, 1, 331–336; N. G. Nossal and L. A. Heppel, Journal of Biological Chemistry, 1966, 241, 13, 3065–3072; R. Bennett, D. R. Taylor and A. Hurst, Biochem. Biophys. Acta, 18(3), 512–521 (1966), and in the collective work Fermentation and enzyme technology, Chap. 12, 239–309, J. Wiley and Sons publishers (1979).

The pellet of cell debris harvested, as a general rule, after centrifugation is resuspended and then brought into contact with a buffer solution containing arginine. The contact time of the suspension of cell debris with the buffer solution containing arginine must be sufficient to permit passage of the protein of interest into the buffer solution. In general, for a temperature of 4° C., the contact time providing for almost complete extraction is 48 hours. Similarly, it was noted that gentle stirring of the biomass in its extraction buffer, thereby avoiding sedimentation of the cell debris, gives higher levels of extraction as a function of time.

This variant of the extraction method according to the invention is suitable for extracting especially periplasmic proteins of interest which are strongly associated with the cell membranes, such as, for example, interleukins.

It is well known to a person skilled in the art that the extraction buffer containing arginine according to the invention may also contain an auxiliary detergent which will have the effect of improving the yield and/or the rate of extraction of the protein of interest. Among auxiliary detergents which may be used, a person skilled in the art will be able to choose from those which enable the advantages of using arginine as extraction agent, especially the retention of the biological activity of the protein of interest, to be preserved. Among these mild auxiliary detergents, there may be mentioned, for example, alkyl glycosides such as alkyl maltosides, nonyl α- or β-D-glycopyranosides, octyl α- or β-D-glycopyranosides or alkylcarbamoylmethyl α- or β-D-glycopyranosides such as, for example, Hecameg®, the very low toxicity of which suggests the possibility of allowing it to appear in trace amounts as formulation agent in the final product.

To carry out the extraction of the protein of interest from the suspension of the pellet of cell debris, it will be preferable to use a buffer solution containing arginine at a concentration of between 0.4M and 2.5M, it being possible for a concentration of 2.5M arginine to be obtained especially in the presence of salts.

Moreover, it was found that arginine exerts a considerable beneficial effect on the yields of secreted recombinant periplasmic protein if it is added at unfamiliar concentrations much higher than those encountered in the culture media manufactured from commercial protein hydrolysates, and which enable the arginine requirements of the strain employed to be covered.

Furthermore, it was found that the beneficial effect exerted by arginine is especially considerable if the arginine concentrations added to the culture medium are between 2 g/l and 10 g/l.

Thus, according to another aspect, the subject of the present invention is a method for the culture of a prokaryotic microorganism transformed by means of an expression vector containing a gene coding for a protein of interest, which consists in culturing the said microorganism in the presence of arginine at a concentration equal to at least 2 g/l, and especially at a concentration of between 2 g/l and 10 g/l.

A person skilled in the art will optimize this arginine concentration for each particular case.

This method is especially suitable for the production of proteins having activity of the cytokine type, especially IL-13, as described in the document EP-A1-0,506,574.

The invention will now be described in greater detail by means of the EXAMPLES below, given only by way of illustration.

EXAMPLE 1

Extraction of periplasmic IL-13 from *E. coli* in the presence of arginine on cell pellet.

1/ Flask culture

In this example, *E. coli* strain RB 791 (Roger Brent, PNAS 78 (1981) pp. 4204–4208), transformed with the plasmid p922 obtained according to methods similar to those defined in Patents EP 360,641 and 356,335 and whose DNA sequence is the sequence SEQ ID NO:1, was used.

The different sequences which constitute this plasmid p922 are shown below.

PROMOTER SEQUENCE (SEQ ID NO:2)

The hexanucleotides TTGCTT and TATAAT characteristic of the promoters in *E. coli* are shown in bold characters XhoI

1   TCGAGTGGGT TTGAGGCGAT CACACTTCTG TTAACGCAGA ACCTAAACGC

51  ATCTCGACTG CACGGTGCAC CAATGCTTCT GGCGTCAGGC AGCCATCGGA

101 AGCTGTGGTA TGGCTGTGCA GGTCGTAAAT CACTGCATAA TTCGTGTCGC

151 TCAAGGCGCA CTCCCGTTCT GGATAATGTT TTTTGCGCCG ACATCATAAC

−35

201 GGTTCTGGCA AATATTCTGA AATGAGCTGT TTCGAGCTGA CTGACTGTTG

−10

251 CTTATATTAC ATCGATAGCG TATAATGTGT GG

SEQUENCE OF THE UNTRANSLATED 5-PRIME REGION OF THE MESSENGER (SEQ ID NO:3)

The ribosome binding site is shown in bold characters. The sequence CAT located at the 3-prime end of this sequence is a portion of the hexanucleotide recognized by the restriction enzyme Nde I

|     |            |            |            |            | RBS        |
| --- | ---------- | ---------- | ---------- | ---------- | ---------- |
| 283 | AATTGTGAGC | GGATAACAAT | TTCACACAGT | TTTTCGCGAA | GAAGGAGATA |
| 333 | TACAT      |            |            |            |            |

SEQUENCE CODING FOR THE IL-13 PRECURSOR (SEQ ID NO:4)

The sequence in italics corresponds to the sequence of mature IL-13. The sequence which is not in bold characters is a linker sequence linking the end of the sequence coding for IL-13 to the hexanucleotide recognized by the restriction enzyme BamH I

| 338 | ATGAAAAAGA | TCCTGGCGTT | AGCTGCGCTG | ACTACCGTTG | TATTCTCTGC |
| --- | ---------- | ---------- | ---------- | ---------- | ---------- |
| 388 | GTCCGCCTTC | GCTGGCCCTG | TGCCTCCCAG | TACTGCCCTC | AGGGAGCTCA |
| 438 | TTGAGGAGCT | GGTCAACATC | ACCCAGAACC | AGAAGGCTCC | GCTCTGCAAT |
| 488 | GGCAGCATGG | TATGGAGCAT | CAACCTGACA | GCTGGCATGT | ACTGTGCAGC |
| 538 | CCTGGAATCC | CTGATCAACG | TGTCAGGCTG | CAGTGCCATC | GAGAAGACCC |
| 588 | AGAGGATGCT | GAGCGGATTC | TGCCCGCACA | AGGTCTCAGC | TGGGCAGTTT |
| 638 | TCCAGCTTGC | ATGTCCGAGA | CACCAAAATC | GAGGTGGCCC | AGTTTGTAAA |
| 688 | GGACCTGCTC | TTACATTTAA | AGAAACTTTT | TCGCGAGGGA | CGGTTCAACT |
| 738 | GAAACTTCGA | AAGCATCATT | ATTTG      |            |            |

TERMINATION SEQUENCES (SEQ ID NO:5)

| 763 | GGATCCGGCT | GCTAACAAAG | CCCGAAAGGA | AGCTGAGTTG | GCTGCTGCCA |
| --- | ---------- | ---------- | ---------- | ---------- | ---------- |

PHAGE T7 GENE 10 TERMINATOR (SEQ ID NO:6)

| 813 | CCGCTGAGCA | ATAACTAGCA | TAACCCCTTG | GGGCCTCTAA | ACGGGTCTTG  |
| --- | ---------- | ---------- | ---------- | ---------- | ----------- |
|     |            |            |            |            | HindIII     |
| 863 | AGGGGTTTTT | TGCTGAAAGG | AGGAACTATA | TCCGGATGTA | CCAAGCTTGG  |
| 913 | CCGGATCAAA | GTTTTGTCGT | CTTTCCAGAC | GTTAGTAAAT | GAATTTTCTG  |
| 963 | TATGAGGTTT | TGCTAAACAA | CTTTCAACAG | TTTCAGCGGA | GTGAGAATAG  |

PHAGE fd TERMINATOR (SEQ ID NO:7)

| 1013 | AAAGGAACAA | CTAAAGGAAT | TGCGAATAAT | AATTTTTTCA | CGTTGAAAAT |
| ---- | ---------- | ---------- | ---------- | ---------- | ---------- |
| 1063 | CTCCAAAAAA | AAAGGCTCCA | AAAGGAGCCT | TTAATTGTAT | CGGTTTATCA |
| 1113 | GCTTGCTTTC | GAGGTGAATT | TCTTAAACAG | CTTGATACCG | ATAGTTGCGC |
| 1163 | CGACAATGAC | AACAACCATC | GCCCACGCAT | AACCGATATA | TTCGGTCGCT |
| 1213 | GAGGCTTGCA | GGGAGTCAAA | GGCCGCTTTT | GCGGGATCGA | T          |

GENE CODING FOR THE LACTOSE OPERON REPRESSOR (SEQ ID NO:8)

```
         SacII
1254  CCGCGGAAGC  ATAAAGTGTA  AAGCCTGGGG  TGCCTAATGA  GTGAGCTAAC
1304  TCACATTAAT  TGCGTTGCGC  TCACTGCCCG  CTTTCCAGTC  GGGAAACCTG
1354  TCGTGCCAGC  TGCATTAATG  AATCGGCCAA  CGCGCGGGGA  GAGGCGGTTT
1404  GCGTATTGGG  CGCCAGGGTG  GTTTTTCTTT  TCACCAGTGA  GACGGGCAAC
1454  AGCTGATTGC  CCTTCACCGC  CTGGCCCTGA  GAGAGTTGCA  GCAAGCGGTC
1504  CACGCTGGTT  TGCCCCAGCA  GGCGAAAATC  CTGTTTGCTG  GTGGTTAACG
1554  GCGGGATATA  ACATGAGCTG  TCTTCGGTAT  CGTCGTATCC  CACTACCGAG
1604  ATATCCGCAC  CAACGCGCAG  CCCGGACTCG  GTAATGGCGC  GCATTGCGCC
1654  CAGCGCCATC  TGATCGTTGG  CAACCAGCAT  CGCAGTGGGA  ACGATGCCCT
1704  CATTCAGCAT  TTGCATGGTT  TGTTGAAAAC  CGGACATGGC  ACTCCAGTCG
1754  CCTTCCCGTT  CCGCTATCGG  CTGAATTTGA  TTGCGAGTGA  GATATTTATG
1804  CCAGCCAGCC  AGACGCAGAC  GCGCCGAGAC  AGAACTTAAT  GGGCCCGCTA
1854  ACAGCGCGAT  TTGCTGGTGA  CCCAATGCGA  CCAGATGCTC  CACGCCCAGT
1904  CGCGTACCGT  CTTCATGGGA  GAAAATAATA  CTGTTGATGG  GTGTCTGGTC
1954  AGAGACATCA  AGAAATAACG  CCGGAACATT  AGTGCAGGCA  GCTTCCACAG
2004  CAATGGCATC  CTGGTCATCC  AGCGGATAGT  TAATGATCAG  CCCACTGACG
2054  CGTTGCGCGA  GAAGATTGTG  CACCGCCGCT  TTACAGGCTT  CGACGCCGCT
2104  TCGTTCTACC  ATCGACACCA  CCACGCTGGC  ACCCAGTTGA  TCGGCGCGAG
2154  ATTTAATCGC  CGCGACAATT  TGCGACGGCG  CGTGCAGGGC  CAGACTGGAG
2204  GTGGCAACGC  CAATCAGCAA  CGACTGTTTG  CCCGCCAGTT  GTTGTGCCAC
2254  GCGGTTGGGA  ATGTAATTCA  GCTCCGCCAT  CGCCGCTTCC  ACTTTTTCCC
2304  GCGTTTTCGC  AGAAACGTGG  CTGGCCTGGT  TCACCACGCG  GGAAACGGTC
2354  TGATAAGAGA  CACCGGCATA  CTCTGCGACA  TCGTATAACG  TTACTGGTTT
2404  CACATTCACC  ACCCTGAATT  GACTCTCTTC  CGGGCGCTAT  CATGCCATAC
2454  CGCGAAAGGT  TTTGCGCCAT  TCGATCTACG  CCGGACGCAT  CGTGGCCGCA
2504  AA
```

SEQUENCE OF pBR 327 (SEQ ID NO:9)

```
         PflmI
2506  CCAACCCTTG  GCAGAACATA  TCCATCGCGT  CCGCCATCTC  CAGCAGCCGC
2556  ACGCGGCGCA  TCTCGGGCCG  CGTTGCTGGC  GTTTTTCCAT  AGGCTCCGCC
2606  CCCCTGACGA  GCATCACAAA  AATCGACGCT  CAAGTCAGAG  GTGGCGAAAC
2656  CCGACAGGAC  TATAAAGATA  CCAGGCGTTT  CCCCCTGGAA  GCTCCCTCGT
2706  GCGCTCTCCT  GTTCCGACCC  TGCCGCTTAC  CGGATACCTG  TCCGCCTTTC
2756  TCCCTTCGGG  AAGCGTGGCG  CTTTCTCAAT  GCTCACGCTG  TAGGTATCTC
2806  AGTTCGGTGT  AGGTCGTTCG  CTCCAAGCTG  GGCTGTGTGC  ACGAACCCCC
2856  CGTTCAGCCC  GACCGCTGCG  CCTTATCCGG  TAACTATCGT            CTTGAGTCCA
2906  ACCCGGTAAG  ACACGACTTA  TCGCCACTGG  CAGCAGCCAC  TGGTAACAGG
2956  ATTAGCAGAG  CGAGGTATGT  AGGCGGTGCT  ACAGAGTTCT  TGAAGTGGTG
3006  GCCTAACTAC  GGCTACACTA  GAAGGACAGT  ATTTGGTATC  TGCGCTCTGC
3056  TGAAGCCAGT  TACCTTCGGA  AAAAGAGTTG  GTAGCTCTTG  ATCCGGCAAA
3106  CAAACCACCG  CTGGTAGCGG  TGGTTTTTTT  GTTTGCAAGC  AGCAGATTAC
3156  GCGCAGAAAA  AAAGGATCTC  AAGAAGATCC  TTFGATCTTT  TCTACGGGGT
3206  CTGACGCTCA  GTGGAACGAA  AACTCACGTT  AAGGGATTTT  GGTCATGAGA
3256  TTATCAAAAA  GGATCTTCAC  CTAGATCCTT  TTAAATTAAA  AATGAAGTTT
3306  TAAATCAATC  TAAAGTATAT  ATGAGTAAAC  TTGGTCTGAC  AGTTACCAAT
3356  GCTTAATCAG  TGAGGCACCT  ATCTCAGCGA  TCTGTCTATT  TCGTTCATCC
3406  ATAGTTGCCT  GACTCCCCGT  CGTGTAGATA  ACTACGATAC  GGGAGGGCTT
3456  ACCATCTGGC  CCCAGTGCTG  CAATGATACC  GCGAGACCCA  CGCTCACCGG
3506  CTCCAGATTT  ATCAGCAATA  AACCAGCCAG  CCGGAAGGGC  CGAGCGCAGA
3556  AGTGGTCCTG  CAACTTTATC  CGCCTCCATC  CAGTCTATTA  ATTGTTGCCG
3606  GGAAGCTAGA  GTAAGTAGTT  CGCCAGTTAA  TAGTTTGCGC  AACGTTGTTG
3656  CCATTGCTGC  AGGCATCGTG  GTGTCACGCT  CGTCGTTTGG  TATGGCTTCA
3706  TTCAGCTCCG  GTTCCCAACG  ATCAAGGCGA  GTTACATGAT  CCCCCATGTT
3756  GTGCAAAAAA  GCGGTTAGCT  CCTTCGGTCC  TCCGATCGTT  GTCAGAAGTA
3806  AGTTGGCCGC  AGTGTTATCA  CTCATGGTTA  TGGCAGCACT  GCATAATTCT
3856  CTTACTGTCA  TGCCATCCGT  AAGATGCTTT  TCTGTGACTG  GTGAGTACTC
3906  AACCAAGTCA  TTCTGAGAAT  AGTGTATGCG  GCGACCGAGT  TGCTCTTGCC
3956  CGGCGTCAAC  ACGGGATAAT  ACCGCGCCAC  ATAGCAGAAC  TTTAAAAGTG
4006  CTCATCATTG  GAAAACGTTC  TTCGGGGCGA  AAACTCTCAA  GGATCTTACC
4056  GCTGTTGAGA  TCCAGTTCGA  TGTAACCCAC  TCGTGCACCC  AACTGATCTT
4106  CAGCATCTTT  TACTTTCACC  AGCGTTTCTG  GGTGAGCAAA  AACAGGAAGG
4156  CAAAATGCCG  CAAAAAAGGG  AATAAGGGCG  ACACGGAAAT  GTTGAATACT
4206  CATACTCTTC  CTTTTTCAAT  ATTATTGAAG  CATTTATCAG  GGTTATTGTC
4256  TCATGAGCGG  ATACATATTT  GAATGTATTT  AGAAAAATAA  ACAAATAGGG
4306  GTTCCGCGCA  CATTTCCCCG  AAAAGTGCCA  CCTGACGTCT  AAGAAACCAT
4356  TATTATCATG  ACATTAACCT  ATAAAAATAG  GCGTATCACG  AGGCCCTTTC
4406  GTCCC
```

(Plasmid pBR 327 is described in Gene, 9, 287–305 (1980))

This strain E. coli RB 791/p922 was set up in preculture overnight at 30° C. with stirring at 200 rpm on L medium (Luria broth described in Molecular Cloning, A Laboratory Manual Sambrook, Fritsch, Maniatis; Cold Spring Harbor Laboratory Press, 2nd edition 1989) containing 100 mg/l of ampicillin. From this preculture, a further flask of L medium was inoculated such that the initial OD (OD=optical density at 600 nm, OD=1 corresponds to 400–450 mg biomass/liter) was 0.6. After waiting for one hour, the culture was induced with 1 mM IPTG (isopropyl β-D-1-thiogalactopyranoside) and culturing was continued for 3 hours. The samples of the bacterial suspension were centrifuged and the bacterial pellets thus recovered were suspended in the extraction buffers below, such that the final OD was 10, this being equivalent to 4.5 g biomass/liter, at the time of extraction.

The extraction buffers used in this example are the following:

A: 0.8M arginine pH 8.0 corrected with HCl in Milli-Q® water (Millipore)

B: 5M guanidine.HCl in Milli-Q® water without pH correction.

Extraction was performed in 1 hour at 4° C. with gentle magnetic stirring.

To measure the efficiency of extraction, samples equivalent to 1 ml of culture suspension with an OD of 0.2 were removed, and the corresponding bacterial pellets obtained by centrifugation at 5,000 g for 10 min were applied to 16.5% polyacrylamide gel after denaturation with SDS. The bacterial suspensions were also centrifuged and their supernatants were desalted by ultrafiltration (Millipore Ultrafree-MC filtration device with a cut-off threshold of 5,000 Da) before being applied to gel. The gel itself was visualized by Western blotting using an anti-CHO IL-13 antibody and quantified with a PhosphorImager® (Molecular Dynamics). The anti-CHO (Chinese hamster ovary) IL-13 antibody used in this example was obtained by immunizing rabbits.

It was found in this example that extraction in the presence of guanidine.HCl or alternatively in the presence of arginine is virtually complete for the mature form, with extraction yields greater than 99% in both cases. It was also noted that, in the supernatant extracted in the presence of arginine, the precursor form of IL-13 is not seen, in distinction to the extract obtained in the presence of guanidine.HCl.

2/Fermenter culture

E. coli strain RB 791/p922 was set up on L medium with 100 mg/l ampicillin and incubated at 30° C. with stirring to constitute a preculture. A 100 ml volume of this preculture was used as inoculum for an MBR brand fermenter of total volume 2.5 liters. Culturing was performed in a volume of 1.2 liters on a medium whose composition is given below and under the conditions defined below.

Medium for fermenter—E. coli strain RB 791/p922

The formula is given for 1 liter final, the volume of the inoculum is to be subtracted.

| 1. Dissolve in 700 ml of Milli-O ® water: | |
|---|---|
| Component | Mass/liter |
| EDTA | 1 g |
| FeSO$_4$.7H$_2$O | 45 mg |
| MgSO$_4$.7H$_2$O | 1.5 g |
| K$_2$SO$_4$ | 0.75 g |
| CaCl$_2$.2H$_2$O | 32 mg |
| NaCl | 1.45 g |
| KCl | 5 g |
| HY-SOY ® | 75 g |

| 1. Dissolve in 700 ml of Milli-O ® water: | |
|---|---|
| Component | Mass/liter |
| L-methionine | 1.4 g |
| Tryptophan | 1 g |
| Trace elements* | 2 ml |
| Yeast extract | 10 g |

Make to 800 ml with Milli-Q® water, autoclave min at 120° C.

| 2. Filter through 0.2 μm in 100 ml of Milli-O ® water: | |
|---|---|
| Glycerol | 15 g |
| K$_2$HPO$_4$ | 7.1 g |

The glycerol concentration will be maintained at between 10 and 15 g/l during culture.

| 3. At the time of induction add: | |
|---|---|
| IPTG | 1 g |
| 6-Aminocaproic acid | 0.65 g |
| HY-SOY ® | 40 g |
| L-cysteine | 0.3 g |

The volume of this addition is not included in the other calculations.

*Solution of trace elements

This is used in the proportion of 1 ml/liter.

For 1 liter of Milli-Q® water final, dissolve in 800 ml:

| | mass/l |
|---|---|
| H$_3$BO$_3$ | 3 mg |
| NaMoO$_4$.2H$_2$O | 4.8 mg |
| MnSO$_4$.H$_2$O | 59 mg |
| CoCl$_2$.6H$_2$O | 23.8 mg |
| CuSO$_4$.5H$_2$O | 8.7 mg |
| ZnSO$_4$.7H$_2$O | 13 mg |
| AlCl$_3$.6H$_2$O | 60 mg |
| KCr(SO$_4$)$_2$.12H$_2$O | 6 mg |
| KI (added at the time of use) | 60 mg |
| NiSO$_4$.6H$_2$O | 2.6 mg |

Add 100 ml of concentrated HCl. Make to 1000 ml with Milli-Q® water.

When the OD has reached 58, the expression of IL-13 is triggered by the addition of IPTG at a concentration of 1 g/l and continued for 5 hours.

The fermenter culture parameters were as follows:

pH=7.4

T=30° C.

pO$_2$=40 mm Hg regulated by stirring, with a flow rate of air of between 1 and 3 liters/min.

The methods of extraction and of measurement of the biological activity which are applied are the same as those described in section 1 above.

It is found that extraction—on a bacterial pellet obtained in a fermenter, no longer in a flask—in the presence of guanidine.HCl or alternatively in the presence of arginine is virtually complete for the mature form of IL-13, with extraction yields of greater than 97% in both cases.

EXAMPLE 2

Biological activity of the IL-13 thus extracted

The extracts obtained in the presence of guanidine.HCl or of arginine in Example 1 were desalted by ultrafiltration as described above. After serial dilution, they were brought into contact with an IL-13-dependent subclone of the B9 cell line. The IL-13 activity of the diluted samples induces the growth of B9 cells, and the half-proliferation concentration was determined. Cell growth was stopped after 3 days of contact by adding MTT (3-(4,5-dimethylthiazol-2-yl)-2,5-diphenyltetrazolium bromide), and measured in a spectrophotometer by the absorption of the blue colouration produced at 565 nm. The IL-13 biological activity was expressed in ng/ml relative to an IL-13 standard which was itself calibrated against the candidate international standard, obtained from an CHO IL-13 culture, obtained by immunizing rabbits according to N. Vita, Archives of Biochemistry and Biophysics, 1983, 225, 2, 436–445.

TABLE II

| Trial on B9 cell line | IL-13 in ng/ml | Biological activity in ng/ml | Specific biological activity |
|---|---|---|---|
| Control | 500 | 500 | 100 |
| Arginine | 3,200 | 1,376 | 43 |
| Guanidine | 4,300 | 1,098 | 25 |

The above results show that the specific biological activity of the arginine extract is, before any other subsequent purification operation, greater than that of the guanidine hydrochloride extract.

EXAMPLE 3

Extraction of periplasmic hGH from *E. coli* in the presence of arginine on cell pellet The strain SEBR 1250 (EP-360,641 and EP-356,335) was set up in preculture overnight at 37° C. with stirring at 200 rpm on L medium (Luria broth) containing 100 mg/l of ampicillin. From this pre-culture, a further flask of L medium was inoculated such that the initial OD was 0.2. After waiting for one hour, the culture was induced with 1 mM IPTG and culturing was continued for 3 hours. The samples of the bacterial suspension were centrifuged, and the bacterial pellets thus recovered were suspended in the extraction buffers such that the final OD was 10, this being equivalent to ~4.5 g biomass/liter, at the time of extraction.

The extraction conditions were as follows:

| Chaotropic agent | pH | T | time |
|---|---|---|---|
| 0.8M Arginine | 8.0 | 22° C. | 20 hours |
| 0.8M Arginine | 8.0 | 4° C. | 20 hours |

To measure the efficacy of extraction, samples equivalent to 1 ml of culture suspension with an OD of 0.2 were removed, and the corresponding bacterial pellets obtained by centrifugation at 5,000 g for 10 minutes were applied to 16.5% polyacrylamide gel after denaturation with SDS. The bacterial suspensions were also centrifuged and their supernatants applied to gel. The gel itself was visualized by Western blotting using an anti-hGH antibody, and quantified with a PhosphorImager® (Molecular Dynamics). The anti-hGH antibodies used were obtained by immunizing rabbits.

Analysis of the bands obtained with the PhosphorImager® enables the conclusion to be drawn that the extraction of human periplasmic hGH produced in *E. coli* in the presence of arginine is efficient. In this example, a yield of at least 60% may be achieved in the presence of 0.8M arginine, pH 8.0, T 22° C. and a period of 20 hours, and an extraction yield of greater than 80% may be achieved in the presence of 0.8M arginine, pH 8.0, T 4° C. and a period of 20 hours.

Since hGH is a hydrophilic protein, it may be concluded from this that recombinant proteins differing greatly in nature, accumulated in the periplasm of *E. coli*, may be extracted simply in the presence of arginine.

EXAMPLE 4

Extraction of periplasmic IL-13 from *E. coli* on cell debris in the presence of arginine 1/ Fermenter culture In this example, *E. coli* strain TP2339 (EP 360,641 and EP 356,335), transformed with plasmid p922 obtained according to methods similar to those defined in EXAMPLE 1 was used.

*E. coli* strain TP2339/p922 was set up on L medium with 100 mg/l ampicillin and incubated at 30° C. with stirring to constitute a preculture. A 100 ml volume of this preculture was used as inoculum for an MBR® brand fermenter of total volume 2.5 liters. Culturing was performed in a volume of 1.2 liters in a medium and under conditions defined below.

Medium for fermenter—*E. coli* strain TP2339/p922

Calculated for a final volume of 1.2 liters, the culture medium consists of the addition of one liter of autoclaved phase and 0.1 liter of filtered phase whose compositions are described below, and of 0.1 liter of preculture defined above.

1/ Autoclaved phase (1000 ml)

Dissolve in 900 ml of Milli-Q® water:

| | Mass/l |
|---|---|
| Tricine | 360 mg |
| $FeSO_4.7H_2O$ | 280 mg |
| $CaCl_2.2H_2O$ | 6.7 mg |
| $MgCl_2.6H_2O$ | 1.27 g |
| $K_2SO_4$ | 8.71 g |
| NaCl | 500 mg |
| KCl | 5 g |
| Hy-Case(SF) ® | 25 g |
| Yeast extract | 18 g |
| Trace elements* | 1 ml |
| L-arginine | 1.5 g |

Adjust the pH to 7.4 with KOH solution and then make to 1000 ml with Milli-Q® water. Autoclave 30 minutes at 120° C.

2/ Filtered phase (100 ml)

Filter under sterile conditions through a 0.2 μm membrane:

| | |
|---|---|
| Glucose | 20 g |
| Glycerol | 50 g |
| $K_2HPO_4$ | 5 g |

The glucose concentration will be maintained during culturing at a concentration of between 5 and 15 g/l.

When the OD has reached 40 (approximately 16 g of dry matter/liter), the expression of IL-13 is triggered by the addition of IPTG at a concentration of 1 g/l and continued for 5 hours. The culture parameters were as follows:

pH=7.4 regulated with 3N HCl and KOH
T=37° C.

$pO_2$=50 mbar regulated by stirring, with a flow rate of air of between 1 and 3 liters/min.

2/ Recovery and grinding of the bacterial bodies

One liter of culture suspension is centrifuged for 20 minutes at −6400 g. The pellet is taken up in the same volume of 10 mM Tris buffer, 1 mM EDTA, 1 mg/l pepstatin, pH 8, with mechanical stirring using a propeller-type paddle.

Grinding is accomplished in a Manton-Gaulin press at a pressure of 700 bars in two runs. The ground preparation as it is may be stored at −80° C. in this example.

3/ Extraction

After thawing, 5 ml of the ground preparation with an OD equal to 75 (30 g of dry matter/liter) are removed and then centrifuged for 50 minutes at 23,300 g.

The pellet thereby obtained is taken up in one third of the initial volume with 0.1 mM Tris buffer, pH 7.0, and then made to the initial volume with a solution containing arginine such that the final arginine concentration is 2.5M and the pH 8.0.

For this example, an auxiliary detergent (Hecameg®) at a final concentration of 20 g/l was combined with the arginine.

The suspension of cell debris made up in this way is placed at 4° C. on a rotary stirrer at 300 rpm for 2 days.

The suspension is then centrifuged a final time for 50 minutes at 23,300 g, the supernatant constituting the expected extract.

4/ Biochemical analysis and analysis of biological activity a) Assay of total proteins was performed by the Biorad® "Protein Assay" method.

b) The method of assay of recombinant IL-13 is that used in Example 1.

Yield of IL-13 thus extracted: the results obtained are described in the following table:

|  | In the suspension of cell debris before extraction | In the supernatant after extraction |
| --- | --- | --- |
| Total proteins | 324 μg/ml | 108 μg/ml |
| Recombinant IL-13 | 575 ng/ml | 390 ng/ml |

It was found in this example that the extraction carried out on cell debris in the presence of 2.5M arginine and an auxiliary detergent enabled an extraction yield of approximately 70% to be obtained.

EXAMPLE 5

Expression of IL-13 in the presence of arginine in the culture medium

*E. coli* strain RB 791/p922 was cultured on L medium with 100 mg/l ampicillin in the presence of different concentrations of arginine. Induction was triggered 1 hour after inoculation by the addition of 1 mM IPTG, and culturing was continued for 3 hours.

The samples of bacterial pellets—equivalent to 1 ml of culture suspension with an OD of 0.2—and the corresponding samples of supernatant were applied to gel, visualized and quantified as described above. The results are given in the table below:

| Sample | OD end of culture | IL-13 in ng/l OD 1 |
| --- | --- | --- |
| Control | 1.17 | 388 |
| Arginine 2 g/l | 1.24 | 455 |
| Arginine 4 g/l | 1.24 | 600 |
| Arginine 8 g/l | 1 | 720 |

It is apparent that, under the experimental conditions and in the expression system in question:

arginine increases the expression of periplasmic IL-13 from 2 g/l, and substantially from 4, g/l growth of the bacterium is slowed down at a concentration of 8 g/l at these concentrations, arginine does not cause leakage of IL-13 into the supernatant.

The value of the arginine extraction method according to the invention is the ability to use protein extracts as they are or with a minimum of treatment in tests of biological activity.

This simplification of the extraction method affords an advantage both for the industrial production of recombinant periplasmic proteins, and for screening by assaying the biological activity on the laboratory scale in relation, for example, to mutated proteins.

In distinction to guanidine.HCl, frequently used as extraction agent, arginine does not attack the materials employed in industry, in particular steels. Furthermore, arginine is a non-polluting agent, which thus does not require an expensive effluent treatment process.

The value of expressing a periplasmic protein in the presence of arginine at concentrations equal to at least 2 g/l, and especially at concentrations of between 2 g/l and 10 g/l, in the culture medium is demonstrated by the increase in the yield of secreted recombinant protein obtained in vivo.

We claim:

1. In a method for the extraction of recombinant periplasmic proteins, wherein the improvement comprises carrying out the extraction in the presence of arginine.

2. A method for the extraction of a periplasmic protein of interest, which comprises the steps of
   (i) culturing a prokaryotic microorganism of the Enterobacteriaceae family transformed with an expression vector containing a gene coding for said protein of interest and means for a periplasmic expression thereof,
   (ii) subjecting the resulting culture to centrifugation or microfiltration thereby producing a cell pellet,
   (iii) suspending the resulting cell pellet in a buffer solution containing arginine thereby producing a suspension,
   (iv) centrifuging the resulting suspension thereby producing a supernatant, and
   (v) recovering the protein of interest from the supernatant thereby obtained.

3. The method according to claim 2, wherein the buffer solution containing arginine is an alkaline aqueous solution having an arginine concentration of at least 0.4M.

4. The method according to claim 2, wherein the protein of interest is IL-13.

5. The method according to claim 2, wherein the protein of interest is hGH.

6. The method according to claim 3, wherein the arginine concentration is between 0.4M and 0.8M.

7. The method according to claim 3, wherein the protein of interest is IL-13.

8. The method according to claim 3, wherein the protein of interest is hGH.

9. A method for the extraction of a periplasmic protein of interest, which comprises the steps of
   (i) culturing a prokaryotic microorganism of the Enterobacteriaceae family transformed with an expression vector containing a gene coding for said protein of interest and means for a periplasmic expression thereof,
   (ii) subjecting the resulting culture to centrifugation or microfiltration thereby producing a cell pellet,
   (iii) lysing the cells from the cell pellet thereby obtained and centrifuging the resulting lysate thereby producing a pellet of cell debris,
   (iv) suspending the pellet of cell debris thereby obtained in a buffer solution containing arginine thereby producing a suspension,
   (v) centrifuging the resulting suspension thereby producing a supernatant, and
   (iv) recovering the protein of interest from the supernatant thereby obtained.

10. The method according to claim 9, wherein the buffer solution containing arginine is an alkaline aqueous solution having an arginine concentration of at least 0.4M.

11. The method according to claim 9, wherein the protein of interest is IL-13.

12. The method according to claim 9, wherein the protein of interest is hGH.

13. The method according to claim 10, wherein the arginine concentration is between 0.4M and 2.5M.

14. The method according to claim 10, wherein the protein of interest is IL-13.

15. The method according to claim 10, wherein the protein of interest is hGH.

16. A method for the culture of a prokaryotic microorganism of the Enterobacteriaceae family transformed with an expression vector containing a gene coding for a protein of interest, which comprises culturing said microorganism in the presence of arginine at a concentration of at least 2 g/l.

17. The method according to claim 16, wherein said arginine concentration is between 2 g/l and 10 g/l.

18. The method according to claim 16, wherein the protein of interest is IL-13.

* * * * *